(12) United States Patent
McKittrick et al.

(10) Patent No.: US 6,458,812 B1
(45) Date of Patent: Oct. 1, 2002

(54) MUSCARINIC ANTAGONISTS

(75) Inventors: Brian A. McKittrick, New Vernon, NJ (US); Guihua Guo, Plainsboro, NJ (US); Zhaoning Zhu, East Windsor, NJ (US); Yuanzan Ye, Iselin, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/023,277

(22) Filed: Dec. 17, 2001

Related U.S. Application Data
(60) Provisional application No. 60/257,853, filed on Dec. 22, 2000.

(51) Int. Cl.[7] .................. A61K 31/445; C07D 211/30; C07D 211/32; C07D 211/60
(52) U.S. Cl. .............. 514/331; 546/230; 546/234; 546/247; 546/186; 546/326; 546/112; 514/316; 514/326
(58) Field of Search ............... 546/234, 247, 546/230, 243, 112, 186; 514/331, 316, 326

(56) References Cited

U.S. PATENT DOCUMENTS

| | | | |
|---|---|---|---|
| 6,037,352 A | 3/2000 | Lowe et al. | 514/316 |
| 6,066,636 A | 5/2000 | Kozlowski et al. | 514/252 |

OTHER PUBLICATIONS

Cheng et al, *Biochem. Pharmacol.*, 22 (1973), p. 3099–3108.

*Primary Examiner*—Alan L. Rotman
*Assistant Examiner*—Janet L Coppins
(74) *Attorney, Agent, or Firm*—Anita W. Magatti

(57) ABSTRACT

Amide derivatives of 1,4 di-substituted piperidine compounds of the formula:

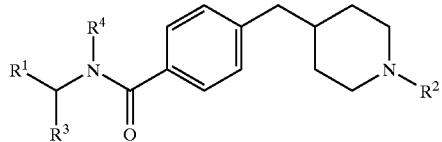

I or a pharmaceutically acceptable salt, ester or solvate thereof, wherein $R^1$ is optionally substituted cycloalkyl, cycloalkylalkyl, aryl, arylalkyl or heteroaryl;

$R^2$ is H, alkyl, or optionally substituted cycloalkyl, cycloalkylalkyl, heterocycloalkyl, bridged cycloalkyl, or bridged heterocycloalkyl;

$R^3$ is alkyl or —$CH_2OH$; and $R^4$ is H or alkyl;

are muscarinic antagonists useful for treating cognitive disorders such as Alzheimer's disease. Pharmaceutical compositions and methods of preparation are also disclosed.

14 Claims, No Drawings

MUSCARINIC ANTAGONISTS

CROSS REFERENCE TO RELATED APPLICATION

This application claims the benefit of U.S. Provisional Application 60/257,853, filed Dec. 22, 2000.

BACKGROUND OF THE INVENTION

The present invention relates to amide derivatives of 1,4-di-substituted piperidines useful in the treatment of cognitive disorders, pharmaceutical compositions containing the compounds, methods of treatment using the compounds, and to the use of said compounds in combination with acetylcholinesterase inhibitors.

Piperidine-derivative muscarinic antagonists useful in the treatment of cognitive disorders such as Alzheimer's disease are disclosed in U.S. Pat. No. 6,037,352. In particular, U.S. Pat. No. 6,037,352 discloses compounds of the generic formula:

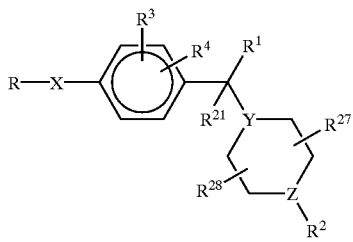

wherein, inter alia, Y is CH; Z is N; X is —NHCO—; R is substituted benzyl; $R^1$ and $R^{21}$ are each H; $R^3$, $R^4$, $R^{27}$ and $R^{28}$ are hydrogen; and $R^2$ is cycloalkyl. Similar compounds wherein the benzene ring is replaced by a pyridinyl ring are disclosed in U.S. Pat. No. 6,066,636. Compounds of the present invention represent a selection invention over U.S. Pat. Nos. 6,037,352 and 6,066,636.

SUMMARY OF THE INVENTION

The present invention relates to compounds of the structural formula I:

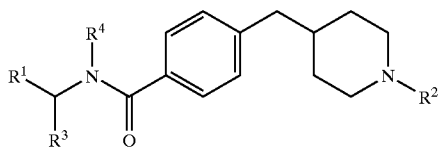

or a pharmaceutically acceptable salt, ester or solvate thereof, wherein $R^1$ is $R^5$—$(C_3–C_8)$cycloalkyl, $R^5$—$(C_3–C_8)$cycloalkyl $(C_1–C_6)$alkyl, $R^5$-aryl, $R^5$-aryl-$(C_1–C_6)$alkyl or $R^5$-heteroaryl;

$R^2$ is H, $(C_1–C_6)$alkyl, $R^6$—$(C_3–C_8)$cycloalkyl, $R^6$—$(C_3–C_8)$cycloalkyl-$(C_1–C_6)$alky, $R^6$-heterocycloalkyl, $R^6$—$(C_6–C_{10})$bridged cycloalkyl, or $R^6$-bridged heterocycloalkyl;

$R^3$ is $C_1–C_6$ alkyl or —$CH_2OH$;

$R^4$ is H or $C_1–C_6$ alkyl;

$R^5$ is 1–4 substituents independently selected from the group consisting of H, $C_1–C_6$ alkyl, halogen, —OH, $C_1–C_6$ alkoxy, $CF_3$, —CN, —$CO_2R^4$, —$CONHR^4$, —$SO_2NHR^4$, —$NHSO_2R^4$ and —$NHC(O)R^4$; and $R^6$ is 1–4 substituents independently selected from the group consisting of H, $C_1–C_6$ alkyl, halogen, —OH, $C_1–C_6$ alkoxy, $CF_3$, —$NH_2$, $(C_1–C_6)$alkylamino, phenyl, $C_1–C_2$ alkylenedioxy, and $(C_1–C_6)$ alkoxycarbonyl.

In another aspect, the invention relates to a pharmaceutical composition comprising a therapeutically effective amount of a compound of formula I in a pharmaceutically acceptable carrier. The invention also relates to a method of using a compound of formula I or a pharmaceutical composition comprising a compound of formula I in the treatment of a cognitive disease or neurodegenerative disease comprising administering an effective amount of a compound or composition of this invention to a mammal in need of such treatment.

In still another aspect, the invention relates to a method for treating a cognitive disease or neurodegenerative disease comprising administering to a mammal in need of such treatment an effective amount of a combination of a compound of formula I and an acetylcholinesterase inhibitor.

In a final aspect, the invention relates to a kit for treating a cognitive disease or neurodegenerative disease comprising in separate containers in a single package pharmaceutical compositions for use in combination, in one container a compound of formula I in a pharmaceutically acceptable carrier and in a second container, an acetylcholinesterase inhibitor in a pharmaceutically acceptable carrier, the combined quantities being an effective amount.

DETAILED DESCRIPTION

Referring to formula I, above, one group of preferred compounds is that wherein $R^1$ is $R^5$-phenyl or $R^5$-cyclohexyl. $R^5$ is preferably H, halogen or $C_1–C_6$ alkyl, more preferably H, F or —$CH_3$.

Another group of preferred compounds is that wherein $R^2$ is $R^6$—$C_3–C_8$ cycloalkyl, especially $R^6$—$C_5–C_7$ cycloalkyl. $R^6$ is preferably H or $C_1–C_6$ alkyl.

$R^3$ is preferably —$CH_3$, and $R^4$ is preferably H.

Compared to the compounds specifically disclosed in U.S. Pat. No. 6,037,352 or U.S. Pat. No. 6,066,636, none of which contain the $R^3$ moiety, compounds of the present invention show greater m2 selectivity.

As used herein, the term "alkyl" represents a straight or branched saturated hydrocarbon chain having the designated number of carbon atoms. If the number of carbon atoms is not specified, e.g., if the term lower alkyl is used, chain lengths of 1 to 6 carbons are intended.

"Cycloalkyl" represents a saturated carbocyclic ring having 3 to 8 carbon atoms. Bridged cycloalkyl refers to cycloalkyl rings wherein two non-adjacent ring members are joined by a $C_1–C_2$ alkyl chain.

The term "heterocycloalkyl " refers to 4- to 7-membered saturated rings comprising 1 to 3 heteroatoms independently selected from the group consisting of —O—, —S—and —$NR^7$—, wherein $R^7$ is H or $C_1–C_6$ alkyl, and wherein the remaining ring members are carbon. Where a heterocyclic ring comprises more than one heteroatom, no rings are formed where there are adjacent oxygen atoms, adjacent sulfur atoms, or three consecutive heteroatoms. Examples of heterocyclic rings are tetrahydrofuranyl, pyrrolidinyl, tetrahydropyranyl, piperidinyl, morpholinyl, thiomorpholinyl and piperazinyl. Bridged heterocycloalkyl refers to heterocycloalkyl rings wherein two non-adjacent carbon ring members are joined by a $C_1$–$C_2$ alkyl chain.

Halogen represents fluoro, chloro, bromo or iodo.

Aryl represents phenyl or naphthyl.

Heteroaryl means a 5 or 6-membered aromatic ring comprising 1 to 3 heteroatoms independently selected from the group consisting of —O—, —S— and —N=, provided that the rings do not include adjacent oxygen and/or sulfur atoms. Examples of heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. All positional isomers are contemplated, e.g., 2-pyridyl, 3-pyridyl and 4-pyridyl.

When a variable appears more than once in the structural formula, for example $R^5$, the identity of each variable appearing more than once may be independently selected from the definition for that variable.

Compounds of the invention have at least one asymmetrical carbon atom, i.e., the carbon to which $R^3$ is attached. All isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I. The preferred stereochemistry of compounds of the invention is shown in formula IA:

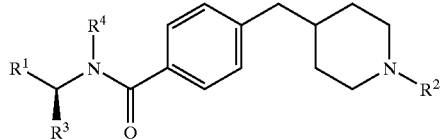

Compounds of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I can be prepared using methods well known to those skilled in the art, for example by procedures disclosed in U.S. Pat. No. 6,037,352, incorporated herein by reference, or by parallel synthesis or combinatorial chemistry. The skilled artisan will recognize that other procedures may be applicable, and that the procedures may be suitably modified to prepare other compounds within the scope of formula I.

Compounds of formula I as defined above are prepared using a solid phase synthetic procedure as shown in the following Scheme 1, wherein Me is methyl and FMOC is 9-fluorenylmethoxycarbonyl.

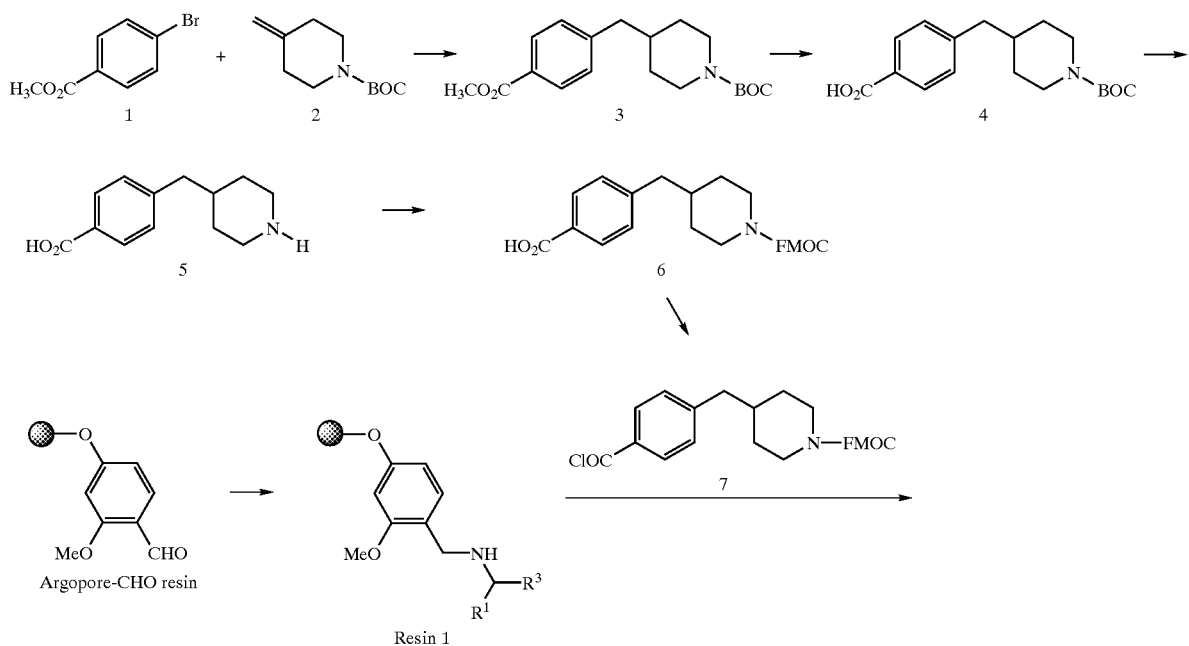

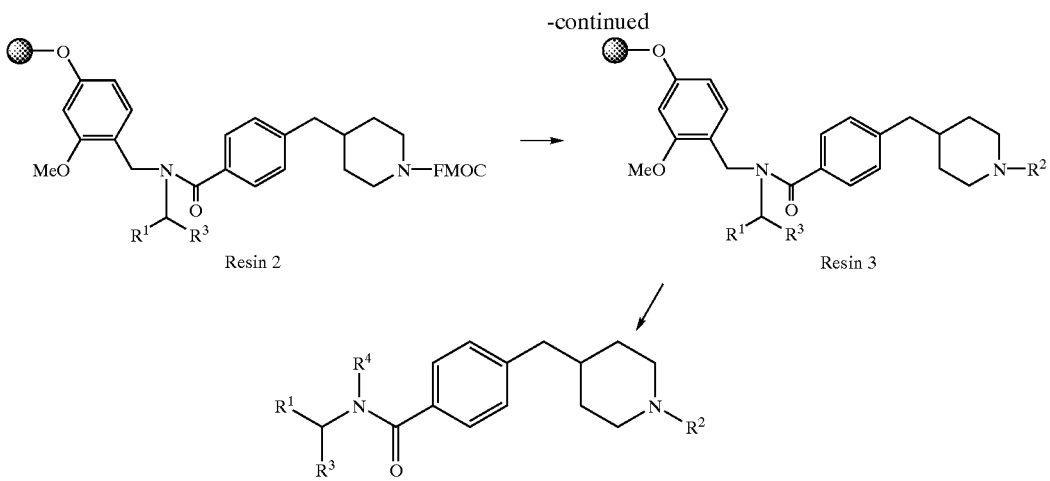

The synthesis in Scheme 1 can be accomplished by the reaction of 9-BBN with an olefin such as 2 followed by the Suzuki coupling with an aryl halide such as 1 to afford compounds 3. Hydrolysis of ester 3 and subsequent removal of the N-Boc provides the amino acid intermediate 5 which is protected by treatment with FmocOSU. This product is then converted into the acid chloride 6 upon treatment with reagents such as $POCl_3$ or oxalyl chloride.

The amine ($R^1CHR^3NH_2$) is reacted with a resin bound aldehyde such as Argopore-MB-CHO resin (Argonaut Corporation, San Carlos, Calif.) by reductive alkylation with sodium triacetoxyborohydride. Subsequent acylation of the resin bound amine (resin 1) with activated acids such as acid chlorides 7, gives resin 2. Deprotection of the N-Fmoc group, followed by reductive alkylation with aldehydes or ketones, or by reaction with an aldehyde followed by treatment with a Grignard reagent, or by reaction with the appropriate mesylate or alkyl halide, provides a resin bound intermediate which, on treatment with TFA, produces compounds of formula I.

Compounds of formula I are also prepared by conventional synthetic chemistry. For example, compounds of formula Ia, wherein $R^1$ is $R^5$-phenyl, $R^3$ is —$CH_3$ and $R^4$ is hydrogen are prepared as shown in Scheme 2:

Scheme 2

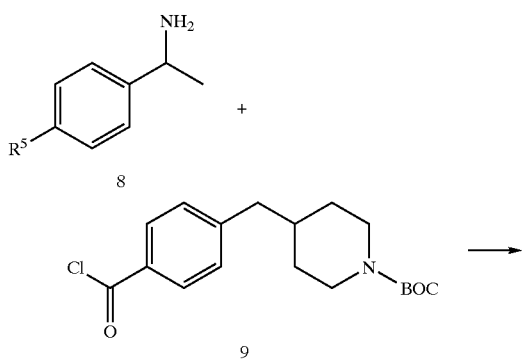

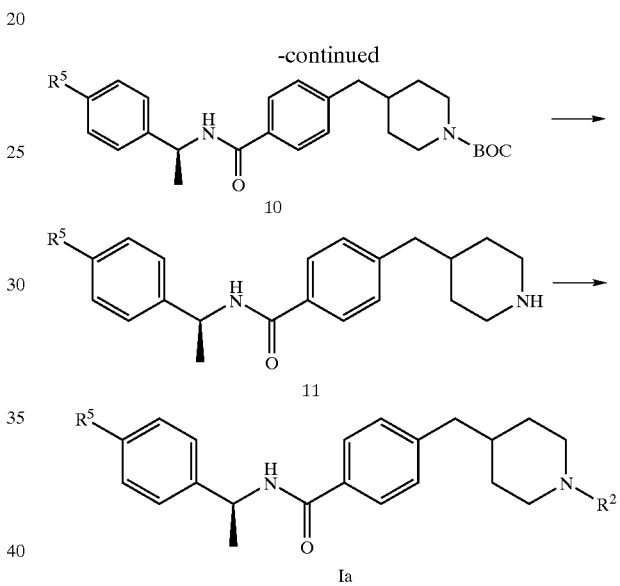

Reaction of amines such as 8 with activated carboxylic acids such as the acid chloride 9 in the presence of a base such as pyridine or triethylamine yields amides of type 10. Treatment of these with an acid such as TFA or HCl gives compounds 11. The piperidine nitrogen of compounds 11 is derivatized to give compounds of type Ia by reductive alkylation with either aldehydes or ketones in the presence of a reducing agent such as sodium triacetoxyborohydride, or alternatively by reaction with an aldehyde followed by treatment with a Grignard reagent. Yet another method involves reaction of the amine 11 with the appropriate mesylate or alkyl halide in the presence of base.

Starting materials of formula 7, 8 and 9 are known in the art, or are prepared by method well known in the art, as are the ketones and aldehydes used to introduce $R^2$ via reductive alkylation or alkylation with alkyl halide or tosylates.

The above reaction may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

The compounds of formula I exhibit selective m2 muscarinic antagonist activity, which has been correlated with pharmaceutical activity for treating cognitive disorders and/or symptoms thereof. Examples of cognitive disorders are Alzheimers disease and senile dementia, with treatment resulting in improvement in memory and learning.

The compounds of formula I display pharmacological activity in test procedures designated to indicate m1 and m2 muscarinic antagonist activity. Following are descriptions of the test procedures.

MUSCARINIC BINDING ACTIVITY

The compound of interest is tested for its ability to inhibit binding to the cloned human m1, m2, m3, m4 and m5 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 μg of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values ($K_i$) were then determined using the following formula (Cheng and Prusoff, 1973);

$$K_i = \frac{IC_{50}}{1 + \left[\frac{\text{concentration of radioligand}}{\text{affinity }(K_D)\text{ of radioligand}}\right]}$$

Hence, a lower value of $K_i$ indicates greater binding affinity.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

MICRODIALYSIS METHODOLOGY

The following procedure is used to show that a compound functions as an m2 antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12,3 mm×0.5 mm) to a depth of 3 mm in striatum beyond the end of the guide. The probe was connected beforehand with tubing to a microinjection pump (CMA/100). Rats were collared, tethered, and, following probe insertion, were placed in a large, clear, plexiglass bowl with litter material and access to food and water. The probe was perfused at 2 μl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 μM neostigmine bromide at pH 7.4). To achieve stable baseline readings, microdialysis was allowed to proceed for 90 minutes prior to the collection of fractions. Fractions (20 μl) were obtained at 10 minute intervals over a 3 hour period using a refrigerated collector (CMA/170 or 200). Four to five baseline fractions were collected, following which the drug or combination of drugs to be tested was administered to the animal. Upon completion of the collection, each rat was autopsied to determine accuracy of probe placement.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic m2 receptor antagonism.

MICROSOMAL STABILITY

A solution of a compound of formula I at a final substrate concentration of 0.5 mg/ml and human, cynomolgus monkey or rat liver microsomes at final P450 concentrations of 0.18, 0.175 and 0.25 nmol/ml, respectively, is incubated in 0.1 M potassium phosphate buffer at pH 7.4 in 96-well micro-titre plates at 37° C. for 3 min in a shaking water bath. A cofactor solution containing $MgCl_2$, Glucose-6-phosphate, NADPH, and Glucose-6-phosphate dehydrogenase is added to each sample (half the total incubation volume/sample) and the total incubation mixture is incubated for 0 and 30 min. (An n=3 samples is incubated for each compound). After each time point, an equal volume of $CH_3CN$ is added. The samples are mixed by vortexing and the plates are centrifuged at 3000 rpm for 20 min. The supernatant is analyzed by Liquid Chromatography Mass Spectrometry (LCMS) for parent drug and/or metabolites using an appropriate analytical method.

For the compounds of this invention, the following ranges of muscarinic antagonistic activity were observed:

m1: 20 to 2000 nM, with preferred compounds being between 200–1000 nM m2: 1 to 500 nM, with preferred compounds being <5 nM, more preferably <10 nM.

In the microsomal stability assay, the compound of Example 2 gave the following results (% remaining after 30 min.): rat—79%; monkey—80%; human—80%.

In the aspect of the invention relating to a combination of a compound of formula I with an acetylcholinesterase inhibitor, examples of acetylcholinesterase inhibitors are donepezil, heptylphysostigmine, tacrine, rivastigmine and galantamine.

For preparing pharmaceutical compositions from the compounds described by this invention, inert, pharmaceutically acceptable carriers can be either solid or liquid.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with an acetylcholinesterase inhibitor to treat cognitive disorders these two active components may be co-administered simultaneously or sequentially, or a single pharmaceutical composition comprising a compound of formula I and an acetylcholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the acetylcholinesterase inhibitor may range from 0.001 to 100 mg/kg body weight.

The invention disclosed herein is exemplified by the following preparation and examples which should not be construed to limit the scope of the disclosure. Alternative mechanistic pathways and analogous structures may be apparent to those skilled in the art. The following terms are abbreviated: room temperature (rt); 9-borabicyclo[3.3.1]nonane (9-BBN); ethyl acetate (EtOAc); trifluoroacetic acid (TFA); tetrahydrofuran (THF); dimethylformamide (DMF); N-(9-fluorenylmethoxycarbonyl)-oxysuccinimide (FMOC-OSuc); 1-(3-dimethylaminopropyl)-3-ethylcarbodiimide hydroch;loride (EDCI); 4-dimethylaminopyridine (DMAP); diethyl azodicarboxylate (DEAD); and dichloroethane (EDC).

Preparation 1

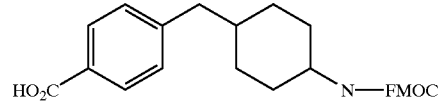

See Scheme 1, above.

Mix starting material (2) (1 g) with 9-BBN (10.2 ml of a 0.5 M THF solution), place under a $N_2$ atmosphere and heat to reflux for 1 h. To the cooled solution add methyl 4-bromobenzoate (1.09 g), $K_2CO_3$ (0.84 g), $PdCl_2$(dppf) (0.21 g), $Ph_3As$ (0.155 gm), DMF (7 ml) and water (1.1 ml) and heat at 65° C. for 3 h. Pour the reaction mixture into ice water, extract into EtOAc and purify the organic layer by flash chromatography (Hex: EtOAc (90:10) to yield compound (3) (1.1 g). Dissolve compound (3) (1.1 g) in $CH_3OH$ (20 ml) and add LiOH (0.2 g) and water (7.5 ml). After heating to reflux for 1 h, cool the reaction mix, remove the $CH_3OH$ under vacuum and acidify the mixture with HCl. Collect the solid by filtration and dry in vacuo to yield compound (4). Dissolve (4) in 4 M HCl in dioxane (35 ml) and stir for 1.5 h. Add ether and collect compound (5) (0.67 g) by filtration. Add compound (5) (0.66 g) to a solution of $Na_2CO_3$ (0.6 g) in water (120 ml) and dioxane (40 ml) followed by dropwise addition at 0° C. of a solution prepared from FMOC-OSuc (0.87 g) and dioxane (10 ml). After 2 h at rt, remove the dioxane under vacuum and acidify the mixture with HCl. Collect the solid by filtration and dry in vacuo to yield compound (6) (0.93 g, LCMS 442.1[M+H]).

PREPARATION 2

See Scheme 1, above

Step 1: Preparation of Resin 1

Combine Argopore-MB-CHO resin (Argonaut Technologies, San Carlos, Calif. 94070) (10 g, 8.1 mmoles) and EDC (45 ml), shake for 5 min, then add 4-fluoro-α-methylbenzylamine (5 g). After shaking for 15 min, add $NaBH(OAc)_3$ (7.5 g) and continue shaking at rt for 20 h. Transfer the reaction mixture to a 250 ml flask and carefully add $CH_3OH$ (50 ml). After the gas evolution ceases, decant the solvent and sequentially wash the resin with 2N $NH_4OH$ in $CH_3OH$ (50 ml), $CH_2Cl_2$ (100 ml), $CH_3OH$ (100 ml) and $CH_2Cl_2$ (2×100 ml). Collect the resin by filtration and dry in a vacuum oven at 40° C.

Step 2: Preparation of Resin 2

Suspend resin 1 from step 1 (2 g) in $CH_2Cl_2$ (10 ml) add DIPEA (1.5 ml) and a $CH_2Cl_2$ solution of acid chloride (7) (10 ml, 0.27 M, prepared from the corresponding acid (6) by reaction with oxalyl chloride in $CH_2Cl_2$ at rt). Shake at rt for 24 h, then filter and wash with $CH_2Cl_2$, $CH_3OH$, THF, $CH_3OH$, and $CH_2Cl_2$ before drying in a vacuum oven at 40° C. overnight.

Step 3: Preparation of Resin 3

Treat resin 2 from step 2 with 20% piperidine in DMF for 20 min. Filter the reaction mixture and repeat this procedure 2 more times, then filter and sequentially wash the resin with THF, $CH_2Cl_2$, $CH_3OH$, and $CH_2Cl_2$, then re-suspend the resin in $CH_2Cl_2$, followed by addition of cyclohexanone (20 eq.) and $NaBH(OAc)_3$ (5 eq.). Shake at rt for 48 h, then filter and wash sequentially with $CH_3OH$, $CH_2Cl_2$, $CH_3OH$, THF, and $CH_2Cl_2$ to provide resin 3.

EXAMPLE 1

General Procedure

Treat resin 3 from Preparation 2, step 3 with 10% TFA in $CH_2Cl_2$ for 1 h. Filter and repeat this procedure. Combine organic layers and concentrate to yield a compound of formula I.

Using this procedure with the appropriate $R^1$—$CH(R^3)$—$NHR^4$ amines and $R_2$-containing aldehydes, ketones, alkyl halides or alkyl tosylates, compounds shown in Table 1 are prepared. The compounds in Table 1 were characterized by Liquid Chromatography-Mass Spectrometry using a Sciex 100 instrument. The flow rate was 1 ml/min. using a C18 column (3.3 cm×4.6 mm id, 3 micron from Supelco) and a gradient of 5% to 95% $CH_3CN$ in water (containing 0.05% TFA) over 10 min. The retention times (Rt) and the observed mass (which corresponds to M+H ) are listed in Table 1.

The compounds prepared have the formula:

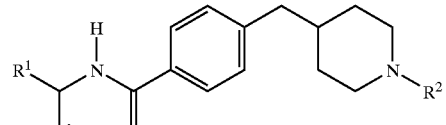

wherein —$CH(R^1)$ ($R^3$) and $R^2$ are as defined in the following Table 1:

-continued
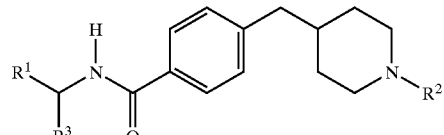
wherein —CH(R¹)(R³) and R² are as defined in the following Table 1:
| Ex. | $\overset{R^1}{\underset{R^3}{\vphantom{X}}}$ | R²— | LCMS R$_t$ | Obs. Mass |
|---|---|---|---|---|
| 1-3 | 1-phenylethyl | cyclohexyl | 5.51 | 405.1 |
| 1-4 | 1-phenylethyl | 3-methylcyclohexyl | 5.71 | 419.1 |
| 1-5 | 1-phenylethyl | isopentyl (4-methylpentyl) | 5.61 | 393.1 |
| 1-6 | 1-phenylethyl | n-propyl | 5.01 | 365.1 |
| 1-7 | 1-phenylethyl | isobutyl | 5.11 | 379.1 |
| 1-8 | 1-phenylethyl | 3-(trifluoromethyl)cyclohexyl | 5.91 | 473.1 |
| 1-9 | 1-phenylethyl | 2-methylbutyl | 5.41 | 393.1 |

-continued
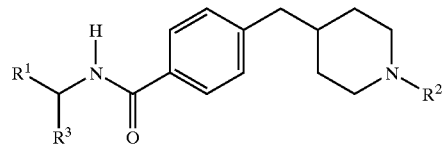
wherein —CH(R¹)(R³) and R² are as defined in the following Table 1:
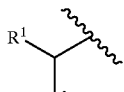
| Ex. | (—CH(R¹)(R³)) | R²— | LCMS $R_t$ | Obs. Mass |
|---|---|---|---|---|
| 1-10 | 1-phenylethyl | cyclohexylmethyl | 5.86 | 419.1 |
| 1-11 | 1-phenylethyl | tetrahydropyran-4-yl | 4.76 | 407.1 |
| 1-12 | 1-phenylethyl | 4-phenylcyclohexyl | 6.41 | 481.1 |
| 1-13 | 1-(4-methylphenyl)ethyl | 4-tert-butylcyclohexyl | 5.31 | 475.1 |
| 1-14 | 1-cyclohexylethyl | 4-tert-butylcyclohexyl | 5.86 | 467.1 |
| 1-15 | 1-phenylpropyl | 4-tert-butylcyclohexyl | 5.36 | 475.1 |

-continued
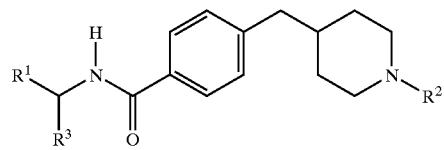
wherein —CH(R¹)(R³) and R² are as defined in the following Table 1:
| Ex. | R¹ R³ | R²— | LCMS R$_t$ | Obs. Mass |
|---|---|---|---|---|
| 1-16 | 4-F-phenyl-CH(CH₃)– | 4-C(CH₃)₃-cyclohexyl | 5.26 | 479.1 |
| 1-17 | 1-naphthyl-CH(CH₃)– | 4-C(CH₃)₃-cyclohexyl | 5.71 | 511.1 |
| 1-18 | 4-CH₃-phenyl-CH(CH₃)– | H₃C-CH₂-CH₂– | 3.76 | 365.1 |
| 1-19 | cyclohexyl-CH(CH₃)– | H₃C-CH₂-CH₂– | 3.76 | 357.1 |
| 1-20 | phenyl-CH(CH₂CH₃)– | H₃C-CH₂-CH₂– | 3.71 | 365.1 |
| 1-21 | H₃C–CH(phenyl)– | H₃C-CH₂-CH₂– | 4.11 | 377.1 |

-continued
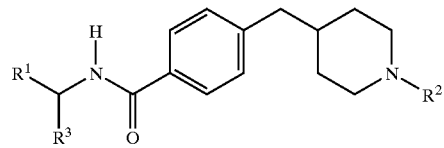
wherein —CH(R$^1$)(R$^3$) and R$^2$ are as defined in the following Table 1:
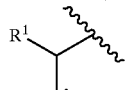
| Ex. | R$^1$ / R$^3$ | R$^2$— | LCMS R$_t$ | Obs. Mass |
|---|---|---|---|---|
| 1-22 | 4-methylphenyl-CH(CH$_3$)- | piperidin-4-yl | 2.5 | 420.1 |
| 1-23 | cyclohexyl-CH(CH$_3$)- | piperidin-4-yl | 2.65 | 412.1 |
| 1-24 | phenyl-CH(CH$_2$CH$_3$)- | piperidin-4-yl | 2.45 | 420.1 |
| 1-25 | 4-fluorophenyl-CH(CH$_3$)- | piperidin-4-yl | 2.4 | 424.1 |
| 1-26 | naphthalen-1-yl-CH(CH$_3$)- | piperidin-4-yl | 2.75 | 456.1 |
| 1-27 | phenyl-CH(CH$_3$)- | piperidin-4-yl | 2.3 | 406.1 |
| 1-28 | 4-methylphenyl-CH(CH$_3$)- | 3-methylcyclohexyl | 4.56 | 433.1 |

-continued
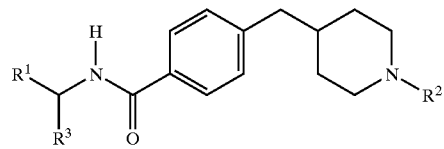
wherein —CH(R$^1$)(R$^3$) and R$^2$ are as defined in the following Table 1:
| Ex. | R$^1$ ⸺ R$^3$ | R$^2$— | LCMS R$_t$ | Obs. Mass |
|---|---|---|---|---|
| 1-29 | H$_3$C—CH(cyclohexyl)— | 3-methylcyclohexyl | 5.01 | 425.1 |
| 1-30 | PhCH(CH$_2$CH$_3$)— | 3-methylcyclohexyl | 4.46 | 433.1 |
| 1-31 | PhCH(CH$_2$OH)— | 3-methylcyclohexyl | 5.16 | 531.1 |
| 1-32 | 4-F-C$_6$H$_4$-CH(CH$_3$)— | 3-methylcyclohexyl | 4.31 | 437.1 |
| 1-33 | 1-naphthyl-CH(CH$_3$)— | 3-methylcyclohexyl | 4.96 | 469.1 |
| 1-34 | H$_3$C—CH(Ph)— | 3-methylcyclohexyl | 4.21 | 419.1 |
| 1-35 | 4-CH$_3$-C$_6$H$_4$-CH(CH$_3$)— | 3-methylcyclohexyl | 4.61 | 433.1 |

-continued
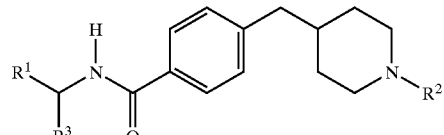
wherein —CH(R¹)(R³) and R² are as defined in the following Table 1:
| Ex. | R¹ / R³ | R²— | LCMS R$_t$ | Obs. Mass |
|---|---|---|---|---|
| 1-36 | H₃C—CH(cyclohexyl)— | H₃C(cyclohexyl) | 5.01 | 425.1 |
| 1-37 | Ph—CH(CH₂CH₃)— | H₃C(cyclohexyl) | 4.56 | 433.1 |
| 1-38 | Ph—CH(CH₂OH)— | H₃C(cyclohexyl) | 3.76 | 435.1 |
| 1-39 | 4-F-C₆H₄—CH(CH₃)— | H₃C(cyclohexyl) | 4.36 | 437.1 |
| 1-40 | 1-naphthyl—CH(CH₃)— | H₃C(cyclohexyl) | 4.86 | 469.1 |
| 1-41 | H₃C—CH(Ph)— | H₃C(cyclohexyl) | 4.26 | 419.1 |
| 1-42 | 4-CH₃-C₆H₄—CH(CH₃)— | tetrahydropyranyl | 3.56 | 421.1 |

-continued
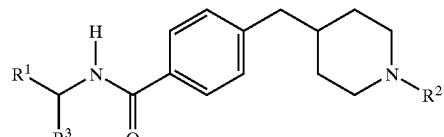
wherein —CH(R¹)(R³) and R² are as defined in the following Table 1:
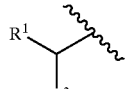
| Ex. | R¹/R³ | R²— | LCMS R$_t$ | Obs. Mass |
|---|---|---|---|---|
| 1-43 | H₃C—CH(cyclohexyl)— | tetrahydropyran-4-yl | 3.36 | 413.1 |
| 1-44 | phenyl-CH(CH₂CH₃)— | tetrahydropyran-4-yl | 3.1 | 421.1 |
| 1-45 | phenyl-CH(CH₂OH)— | tetrahydropyran-4-yl | 4.21 | 519.1 |
| 1-46 | 4-F-phenyl-CH(CH₃)— | tetrahydropyran-4-yl | 2.9 | 425.1 |
| 1-47 | 1-naphthyl-CH(CH₃)— | tetrahydropyran-4-yl | 4.16 | 457.1 |
| 1-48 | H₃C—CH(phenyl)— | tetrahydropyran-4-yl | 2.85 | 407.1 |
| 1-49 | 4-CH₃-phenyl-CH(CH₃)— | cyclohexyl | 4.36 | 419.1 |

-continued
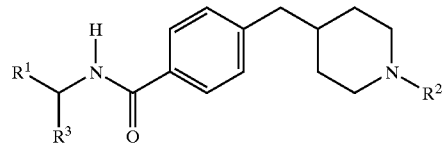
wherein —CH(R¹)(R³) and R² are as defined in the following Table 1:
| Ex. | R¹/R³ | R²— | LCMS R$_t$ | Obs. Mass |
|---|---|---|---|---|
| 1-50 | H₃C—CH—(cyclohexyl) | cyclohexyl | 4.61 | 411.1 |
| 1-51 | phenyl—CH(CH₃)— | cyclohexyl | 4.21 | 419.1 |
| 1-52 | 4-F-phenyl—CH(CH₃)— | cyclohexyl | 3.96 | 423.1 |
| 1-53 | 1-naphthyl—CH(CH₃)— | cyclohexyl | 4.81 | 455.1 |
| 1-54 | H₃C—CH—(phenyl) | cyclohexyl | 4.41 | 405.1 |
| 1-55 | 4-CH₃-phenyl—CH(CH₃)— | cyclopentyl | 4.11 | 405.1 |
| 1-56 | H₃C—CH—(cyclohexyl) | cyclopentyl | 4.46 | 397.1 |

-continued
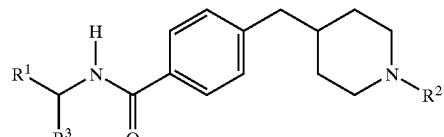
wherein —CH(R¹)(R³) and R² are as defined in the following Table 1:
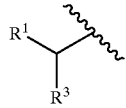
| Ex. | R¹ R³ | R²— | LCMS $R_t$ | Obs. Mass |
|---|---|---|---|---|
| 1-57 | (2-phenylethyl, CH₃) | cyclopentyl | 4.01 | 405.1 |
| 1-58 | (2-phenyl-1-hydroxymethyl) | cyclopentyl | 4.76 | 503.1 |
| 1-59 | (1-(4-fluorophenyl)ethyl) | cyclopentyl | 5.56 | 409.1 |
| 1-60 | (1-(naphthalen-1-yl)ethyl) | cyclopentyl | 6.26 | 441.1 |
| 1-61 | (1-phenylethyl) | cyclopentyl | 5.36 | 391.1 |
| 1-62 | (1-cyclohexylethyl) | N-methylpiperidin-4-yl | 4.91 | 426.1 |
| 1-63 | (1-(4-methylphenyl)ethyl) | H | 5.21 | 337.1 |

-continued
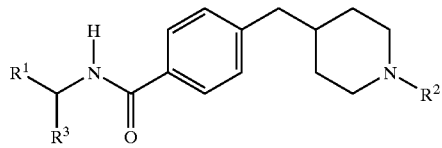
wherein —CH($R^1$) ($R^3$) and $R^2$ are as defined in the following Table 1:
| Ex. | $R^1$ ⋎ $R^3$ | $R^2$— | LCMS $R_t$ | Obs. Mass |
|---|---|---|---|---|
| 1-64 | H₃C⋎ (cyclohexyl) | H | 5.51 | 329.1 |
| 1-65 | phenyl-CH(CH₂CH₃)- | H | 5.11 | 337.1 |
| 1-66 | 4-F-phenyl-CH(CH₃)- | H | 4.86 | 341.1 |
| 1-67 | 1-naphthyl-CH(CH₃)- | H | 5.66 | 373.1 |
| 1-68 | H₃C-CH(phenyl)- | H | 4.51 | 323.1 |
| 1-69 | (4-F-phenyl)-CH(CH₃)- | H₃C-CH(CH₂CH₃)- | 6.91 | 451.1 |
| 1-70 | (4-F-phenyl)-CH(CH₃)- | -CH₂CH₃ | 5.66 | 369.1 |

-continued
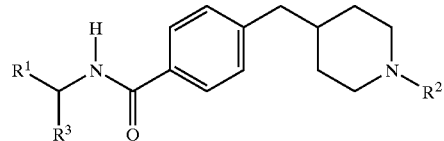
wherein —CH(R¹)(R³) and R² are as defined in the following Table 1:
| Ex. | R¹⟋R³ | R²— | LCMS $R_t$ | Obs. Mass |
|---|---|---|---|---|
| 1-71 | 4-F-C₆H₄-CH(CH₃)- | 4-methylcyclohexyl | 6.61 | 437.1 |
| 1-72 | 4-F-C₆H₄-CH(CH₃)- | trans-4-hydroxycyclohexyl | 5.06 | 439.1 |
| 1-73 | 4-F-C₆H₄-CH(CH₃)- | 1,4-dioxaspiro[4.5]dec-8-yl | 5.06 | 482.1 |
| 1-74 | 4-F-C₆H₄-CH(CH₃)- | 4-oxocyclohexyl | 5.16 | 437.1 |
| 1-75 | 4-F-C₆H₄-CH(CH₃)- | trans-2-hydroxycyclohexyl | 6.11 | 439.1 |
| 1-76 | 4-F-C₆H₄-CH(CH₃)- | cis-2-hydroxycyclohexyl | 5.91 | 439.1 |
| 1-77 | 4-F-C₆H₄-CH(CH₃)- | 4-fluorocyclohexyl | 5.66 | 441.1 |

-continued
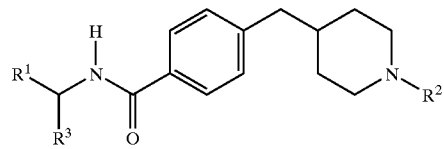
wherein —CH(R¹)(R³) and R² are as defined in the following Table 1:
| Ex. | R¹ ⌇⌇ R³ | R²— | LCMS R_t | Obs. Mass |
|---|---|---|---|---|
| 1-78 | 4-F-C₆H₄-CH(CH₃)– | H | 5.06 | 437.1 |
| 1-79 | 4-F-C₆H₄-CH(CH₃)– | –CH(CH₃)₂ | 5.16 | 383.1 |
| 1-80 | 4-F-C₆H₄-CH(CH₃)– | 3,3,5-trimethylcyclohexyl | 7.16 | 479.1 |
| 1-81 | 4-F-C₆H₄-CH(CH₃)– | bicyclo[2.2.2]octyl | 6.06 | 449.1 |
| 1-82 | 4-F-C₆H₄-CH(CH₃)– | –CH(CH₂CH₃)₂ | 6.16 | 411.1 |
| 1-83 | 4-F-C₆H₄-CH(CH₃)– | N-methyl-tropanyl | 4.71 | 464.1 |

-continued

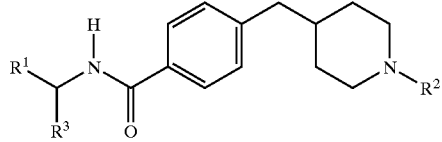

wherein —CH(R¹) (R³) and R² are as defined in the following Table 1:

| Ex. |  R¹ / R³ | R²— | LCMS R_t | Obs. Mass |
|---|---|---|---|---|
| 1-84 | CH₃, 4-F-phenyl | 4-CF₃-cyclohexyl | 4.01 | 491.1 |

EXAMPLE 2

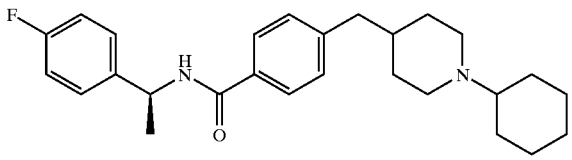

Step 1: (R)-p-Fluoro-α-methylbenzylalcohol

To a cooled solution (0° C.) of p-fluoroacetophenone (13.8 g, 0.1 mol) and (S)-3,3-diphenyl-1-methyltetrahydro-3H-pyrrolo-[1,2-c][1,3,2]oxazaborole (30 ml of a 2M solution in toluene) in anhydrous THF (400 ml) under $N_2$ was added borane dimethylsulfide (14 ml, 0.14 mol). The solution was stirred at 0° C. for 30 min, then $CH_3OH$ (50 ml) was added, followed by washing with 1 M HCl, water, saturated $NaHCO_3$ and drying over anhydrous $Na_2SO_4$. The solvent was evaporated to give 13.5 g (R)-p-fluroro-α-methylbenzylalcohol.

Anal Data: ¹H NMR ($CDCl_3$), δ 7.35 (d, 2H), δ 7.1 (t, 2H), δ 4.9 (q, 1H), δ 1.45 (d, 3H). HPLC: (Chiralpak AS column, 10% isopropanol in hexane, flow rate 1 ml/min) 5.68 min R isomer 98%; 6.10 min, S isomer 2%.

Step 2: (S)-p-Fluoro-α-methylbenzylazide

To a cooled solution (−15° C.) of the product of Step 1 (23.5 g, 0.168 mol) in toluene (300 ml) was added diphenylphosporyl azide (55.4 g, 0.395 mol) followed by DBU (30.4 ml, 0.2 mol). After stirring overnight, the resulting biphasic solution was poured into 500 ml 1 N HCl. The aqueous layer was extracted with toluene and the combined organic layers were washed with water, 1 N HCl and dried over $Na_2SO_4$. After removal of solvent, 25 g of crude product was obtained and was carried on to next step without further purification.

Step 3: (S)-p-Fluoro-α-methylbenzylamine

A mixture of the crude product of Step 2 (1.2 g, 7.3 mmol), conc. HCl (1 ml in 50 ml $CH_3OH$) and Pd/C (10% w/w) (140 mg) was hydrogenated at 60 psi for 4 hr. After removal of the solvent, the residue was redissolved in 20 ml water and washed with ether. The aqueous layer was then basified to pH 11 and extracted with ether. The ether solution was dried and solvent evaporated to give 1.1 gram of (S)-p-fluoro-α-methylbenzylamine.

Anal Data: ¹H NMR($CDCl_3$), δ 7.3 (dd 2H), δ 7.05 (t, 2H), δ 4.8 (q, 1H), δ 1.5 (d, 3H). HPLC: (Chiralpak CR(+) column, perchloric acid in water pH 1.5, flow rate 1 ml/min) 31.8 min S isomer 97.5%; 43.2 min, R isomer 2.5%.

Step 4: N-[1-(S)-p-fluorophenethyl]-4-(4'-piperidinylmethyl)benzamide

To a solution of the product of Step 3 (4.8 g, 34.5 mmol), 4-(N-Boc-piperidinylmethyl)-benzoic acid (10 g, 31.3 mmol) and DMAP (0.38 g, 3.1 mmol) in $CH_2Cl_2$ was added EDCl hydrochloride (6.1 g, 34.4 mmol) and the final solution was stirred for 2 h before being quenched with 0.5 N HCl. The mixture was extracted with $CH_2Cl_2$ and washed with water. After removal of solvent, the residue was dissolved in TFA (10 ml) for 30 min. After removal of the acid, the residue was chromatographed to give 10.2 gram of desired product.

Anal Data: ¹H NMR ($CD_3OD$), δ 7.76 (d, 2H), δ 7.40 (dd, 2H), δ 7.25 (dd, 2H), δ 7.05 (t, 2H), δ 5.2 (q, 1H), δ 2.95 (m, 2H), δ 2.59 (m, 2H), δ 2.5 (m, 2H), δ 1.65 (m, 1H), δ 1.6 (m, 2H), δ 1.55 (d, 3H), δ 1.95 (m, 2H).

Step 5:

To a solution of the product of Step 4 (7.5 grams, 22 mmol) in DCE (250 ml) was added cyclohexanone (3.24 g, 33 mmol) and sodium triacetoxyborohydride (7.01 g, 33 mmol). After the final mixture was stirred overnight, it was poured into 1 N HCl and the solution washed with ether. The aqueous layer was basified with NaOH to pH 11 and extracted with $CH_2Cl_2$. The organic layer was dried, the solvent evaporated and the residue chromatographed to give 8.5 g of the title compound.

Anal Data: ¹H NMR ($CD_3OD$): δ 7.668 (d, 2H), δ 7.354 (q, 2H), δ 7.186 (d, 2H), δ 7.028 (t, 2H), δ 5.309 (m, 1H), δ 2.858 (d,2H), δ 2.565 (d, 2H), δ 2.231 (m, 1H), δ 2.105 (td, 2H), δ 1.86–1.75 (m, 4H), δ 1.614 (m, 2H), δ 1.58 (d, 3H), δ 1.56–1.42 (m, 3H), δ 1.32–1.02 (m, 6H). $[\alpha]_{D/20}$ 19.8 in MeOH. $C^{13}$ ($CDC^{13}$) δ 167.4, 164.2, 161.7, 145.9, 140.0, 132.9, 130.3, 128.9, 128.8, 127.8, 116.6, 116.4, 65.1, 50.4, 49.7, 44.4, 39.5, 33.9, 30.1, 27.6, 27.4, 23.1 ES-LCMS, 6.36 min, LC area 100%, M+1, 423. Melting Point (HCl Salt): 234–235° C.

EXAMPLE 3

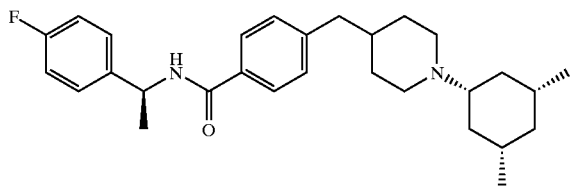

To a solution of t,t-3,5-dimethylcyclohexyl-p-toluenesulfonate (1.35 g, 4.61 mmol) in 4-methyl-2-pentanone (5 ml) was added the product of Example 2, Step 4 (0.522 g, 1.537 mmol) and $Na_2CO_3$ (3.26 g, 30.74 mmol) and the mixture was refluxed overnight. The final reaction mixture was filtered and the solid washed with $CH_2Cl_2$ The combined organic layer was concentrated and the residue was chromatographed using a mixture of 5%v/v 2M $NH_3$ in $CH_3OH$ with $CH_2Cl_2$ to give 420 mg of the title compound.

Anal Data: $^1H$ NMR($CDCl_3$): δ 7.75 (d, 2H), δ 7.40 (q, 2H), δ 7.248 (d,2H), δ 7.046 (t, 2H), δ 5.217 (q, 1H), δ 2.918 (d, 2H),2.597 (d,2H), δ 2.408 (tt, 1H), δ 2.241 (t, 2H), δ 1.835 (d, 2H), δ 1.7–1.57 (m, 3H), δ 1.542 (d, 3H), δ 1.5–1.22 (m,6H), δ 0.92 (d, 6H), δ 0.835 (q, 1H), δ 0.498 (q, 1H).

EXAMPLE 4

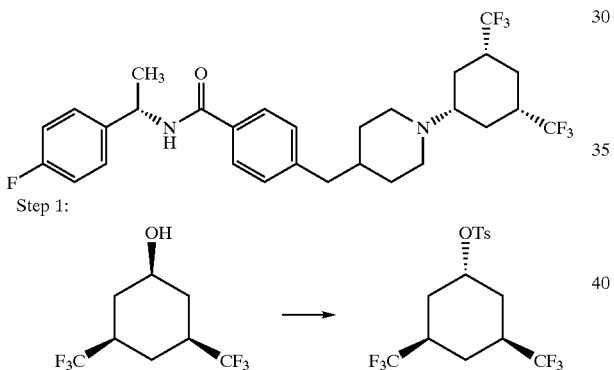

Step 1:

To a solution of c,c-3,5-bis-trifluoromethylcyclohexanol (0.2 g, 0.85 mmol) in anhydrous benzene (8 ml) was added triphenylphosphine (0.33 g, 1.27 mmol) followed by DEAD (0.22g, 1.27 mmol). The solution was stirred at rt for 5 min. before methyltosylate (0.236 g, 1.27 mmol) was added. After the reaction was stirred at rt for 72 h, it was diluted with ether (80 ml), washed with water, 1 N HCl, water and sat. $NaHCO_3$, brine and dried over anhydrous $MgSO_4$. The organic solvent was evaporated and the residue chromatographed in a silica gel column eluted with 10% EtOAc in hexane to give 0.28 g of the desired tosylate (85% yield). $H^1$ NMR ($CDCl_3$): δ 7.8 (d, 2H), δ 7.4 (d, 2H), δ 5.0 (b, 1H), δ 2.5 (m, 2H), δ 2.45 (s, 3H), δ 2.18 (m, 3H), δ 1.45 (m, 2H), δ 1.35 (m, 1H).

Step 2:

Following the same procedure for Example 3, and using the tosylate from step 1, the title compound was prepared. $H^1$ NMR($CDCl_3$): δ 7.65 (d, 2H), δ 7.35 (m, 2H), δ 7.2 (d, 2H), δ 7.0 (m, 2H), δ 5.3 (m, 1H), δ 2.8 (m, 2H), δ 2.6 (d, 2H), δ 2.45 (m, 1H), δ 2.05–2.25 (m, 6H), δ 1.45–1.8 (m, 4H), δ 1.6 (d, 3H), δ 1.2–1.4 (m, 5H). ES-LCMS, Rt 6.11 min., observed mass, 559 (M+H).

EXAMPLE 5

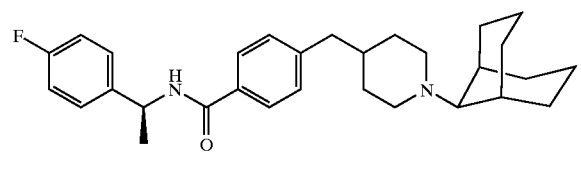

To a solution of the product of Example 2, Step 4 (2.46 g, 7.2 mmol) in DCE (75 ml) was added bicyclo[3,3,1]nonan-9-one (1.0 g, 7.2 mmol) and sodium triacetoxyborohydride (3.24 g, 14 mmol). After the final mixture was stirred overnight, the solvent was evaporated and the residue chromatographed to give 0.640 g of the title compound.

Anal Data: $^1H$ NMR($CD_3OD$): δ 7.675 (d, 2H), δ 7.360 (q,2H), δ 7.194 (d, 2H), δ 7.027 (t, 2H), δ 5.309 (m, 1H), δ 3.07 (d, 2H), δ 2.56 (d,2H), δ 2.00–1.66 (m, 1H), δ 1.58 (d, 3H), δ 1.54–1.43 (m, 7H), δ 1.33–1.23 (m, 4H).

EXAMPLE 6

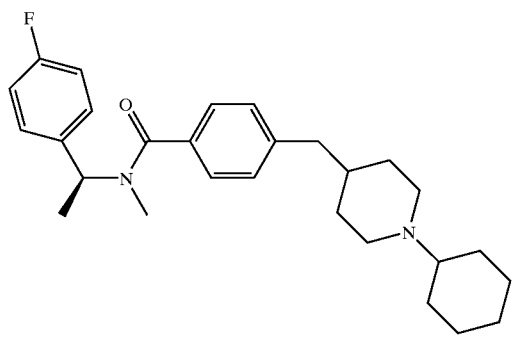

Under $N_2$, NaH (57.6 mg, 2.4 mmol) was suspended in DMF, followed by addition, with stirring, of a DMF solution of the compound prepared in Example 2 (100 mg, 0.24 mmol). After 30 min., $CH_3I$ (0.017 ml, 0.264 mmol) was added and the mixture was stirred for 40 h. The mixture was poured into an ice-$H_2O$ bath, the precipitate was collected by filtration, and the solid was washed with water and dried under vacuum to yield 100 mg of the title compound. LCMS: Rt 6.81 min. observed mass 437 (M+H).

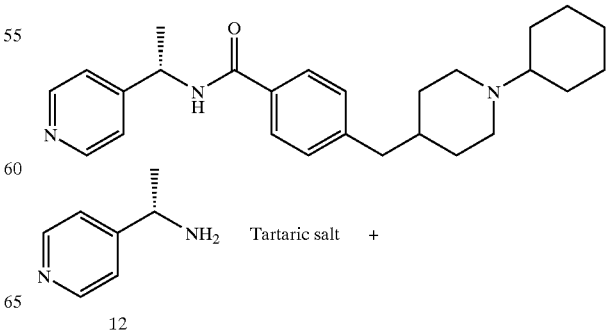

12

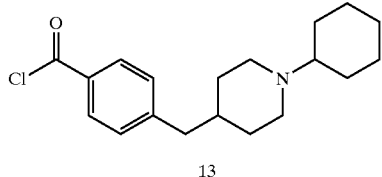

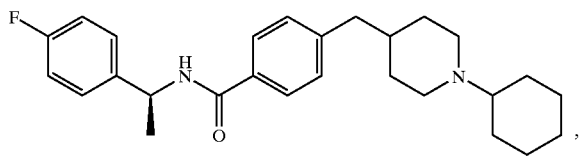

To a solution of 12 (0.91 mmol) in a mixture of 1:1 H₂O/sat. Na₂CO₃ (10 ml) was added 13 (2mmol) in CH₂Cl₂ (2ml) solution under vigorous stirring. After 1 h, the organic layer was separated and the aqueous layer washed with CH₂Cl₂ 3 times. The ct.5 ombined organic solution was washed with sat. Na₂CO₃ and brine, then dried with Na₂SO₄. After removal of solvent, the residue was purified through a semi-preparative HPLC column eluting with 2% (v/v) 7N NH₃ in CH₃OH in CH₂Cl₂ to give 140 mg of the desired product.

H$^1$ NMR (CDCl₃) δ 8.55, d, 2H, δ 7.7, d 2H, δ 7.26 d, 2H, δ 7.20 d, 2H; δ 6.45 d, 1H; δ 5.3, m, 1H; δ 2.859 m2H; δ 2.58, d, 2H; δ 2.25, m, 1H; δ 2.1, m, 2H; δ 1.7–1.9, m, 4H; δ 1.4–1.65, m, 7H; δ 1.0–1.35, m; 6H. LCMS: C18 reverse phase column, 5%–95% gradient of CH₃CN/water in 10 min. Ret. Time 3.58 min. obs. M+1 406.

What is claimed:

1. A compound having the structural formula:

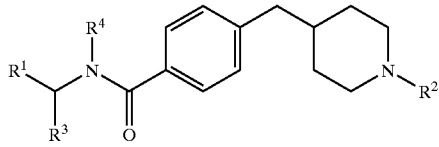

I or a pharmaceutically acceptable salt, ester or solvate thereof, wherein

- $R^1$ is $R^5$—(C₃–C₈)cycloalkyl, $R^5$—(C₃–C₈)cycloalkyl (C₁–C₆)alkyl, $R^5$-aryl, or $R^5$-aryl-(C₁–C₆)alkyl;
- $R^2$ is H, (C₁–C₆)alkyl, $R^6$—(C₃–C₈)cycloalkyl, $R^6$—(C₃–C₈)cycloalkyl-(C₁–C₆)alkyl, or $R^6$—(C₆–C₁₀) bridged cycloalkyl;
- $R^3$ is C₁–C₆ alkyl or —CH₂OH;
- $R^4$ is H or C₁–C₆ alkyl;
- $R^5$ is 1–4 substituents independently selected from the group consisting of H, C₁–C₆ alkyl, halogen, —OH, C₁–C₆ alkoxy, CF₃, —CN, —CO₂$R^4$, —CONHR$^4$,—SO₂NHR$^4$, —NHSO₂$R^4$ and —NHC(O)$R^4$; and
- $R^6$ is 1–4 substituents independently selected from the group consisting of H, C₁–C₆ alkyl, halogen, —OH, C₁–C₆ alkoxy, CF₃, —NH₂, (C₁–C₆)alkylamino, phenyl, C₁–C₂ alkylenedioxy, and (C₁–C₆) alkoxycarbonyl.

2. A compound of claim 1 wherein $R^1$ is $R^5$-phenyl or $R^5$-cyclohexyl.

3. A compound of claim 2 wherein $R^5$ is H, halogen or C₁–C₆ alkyl.

4. A compound of claim 3 wherein $R^5$ is H, F or —CH₃.

5. A compound of claim 1 wherein $R^2$ is $R^6$—C₃–C₈ cycloalkyl.

6. A compound of claim 1 wherein $R^2$ is $R^6$—C₅–C₇cycloalkyl.

7. A compound of claim 5 wherein $R^6$ is H or C₁–C₆ alkyl.

8. A compound of claim 1 wherein $R^3$ is —CH₃.

9. A compound of claim 1 wherein $R^4$ is H.

10. A compound of claim 1 selected from the group consisting of

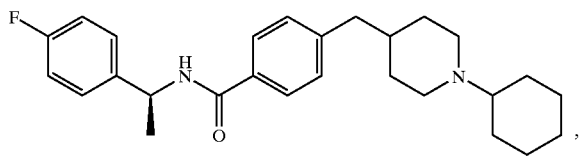

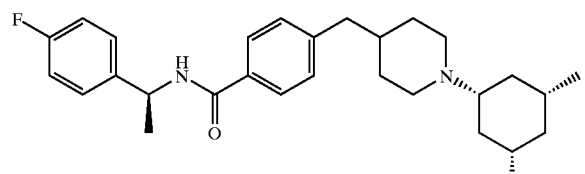

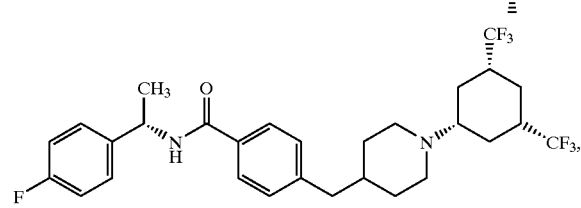

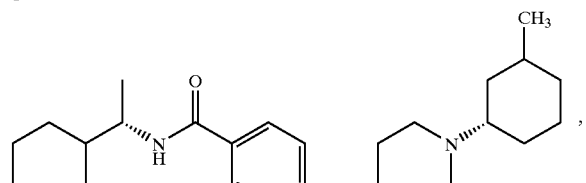

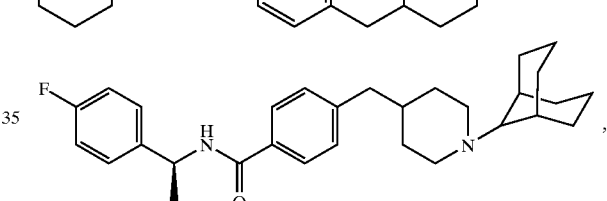

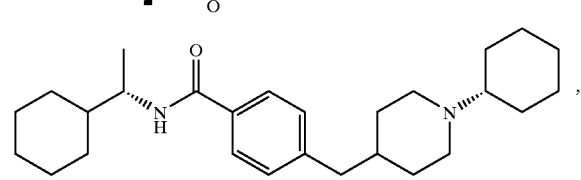

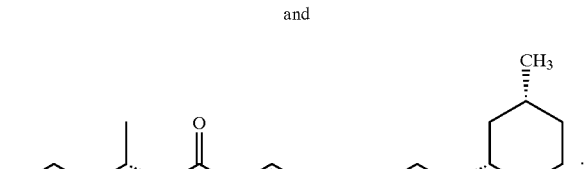

and

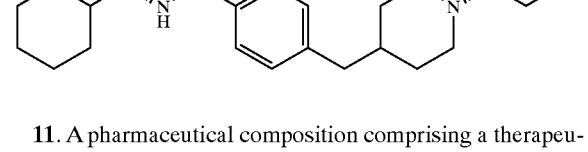

11. A pharmaceutical composition comprising a therapeutically effective amount of a compound of claim 1 in combination with a pharmaceutically acceptable carrier.

12. A method for improving cognition in mammals comprising administering an effective amount of a compound of claim 1.

13. A method for improving cognition in mammals comprising administering an effective amount of a combination of a compound of claim 1 with an acetylcholinesterase inhibitor.

14. A kit for improving cognition in mammals comprising in separate containers in a single package pharmaceutical compounds for use in combination, in one container a compound in accordance with claim 1 and in a separate container an acetylcholinesterase inhibitor, said compound and inhibitor each being in a pharmaceutically acceptable carrier and their combined quantities being an effective amount.

* * * * *